United States Patent

Tomcufcik et al.

[11] Patent Number: 4,767,749
[45] Date of Patent: Aug. 30, 1988

[54] ESTER OF (TRIARYLPHOSPHORANYLIDENE)CARBAMIC ACID HAVING DIURETIC AND ABILITY TO LOWER PLASMA RENIN PROPERTIES

[75] Inventors: Andrew S. Tomcufcik, Old Tappan; John E. Emma, New City; Nancy H. Eudy, Cornwall-on-Hudson; Joseph W. Marsico, Pearl River; Howard Newman, Monsey, all of N.Y.

[73] Assignee: American Cyanamid Company, Stamford, Conn.

[21] Appl. No.: 888,613

[22] Filed: Jul. 23, 1986

[51] Int. Cl.[4] ............... C07C 125/06; A61K 31/66
[52] U.S. Cl. ......................... 514/137; 546/22; 548/112; 549/222; 560/27; 514/89; 514/99
[58] Field of Search ............. 560/27; 514/137

[56] References Cited

FOREIGN PATENT DOCUMENTS 137716 9/1979 German Democratic Rep. ... 560/27

Primary Examiner—Alan L. Rotman
Attorney, Agent, or Firm—H. G. Jackson

[57] ABSTRACT

Novel triarylphosphinimide derivatives having the formula

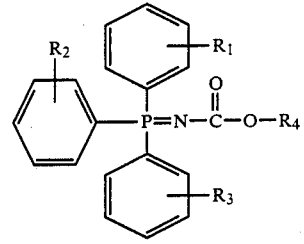

wherein $R_1$, $R_2$ and $R_3$ are each at the ortho or meta position, represent mono- or disubstituents and are selected from the group consisting of hydrogen, alkyl($C_1$–$C_3$), alkoxy($C_1$–$C_3$), trifluoromethyl and halogen; and $R_4$ is selected from the group consisting of alkyl($C_1$–$C_3$), alkenyl($C_2$–$C_3$), alkynyl($C_2$–$C_4$), cycloalkyl($C_3$–$C_5$), cycloalkyl($C_3$–$C_6$)methyl, 4-oxopentyl, 3-tetrahydrofuranyl, 2,3-dihydro-1H-inden-1-yl, 1-alkyl($C_1$–$C_3$)cyclopentyl, trans-2-alkyl($C_1$–$C_3$)cyclopentyl, trans-2-alkoxy($C_1$–$C_3$)cyclopentyl, 1-cyclopropylethyl, 2-methylcyclopropylmethyl, dicyclopropylmethyl, 2-, 3- or 4-pyridinylmethyl, 2-cyclopenten-1-yl, tetrahydro-2H-pyran-4-yl and cis and trans-2-methoxycyclohexyl; with the proviso that when $R_4$ is alkyl($C_1$–$C_3$), $R_1$, $R_2$ and $R_3$ may not each be hydrogen

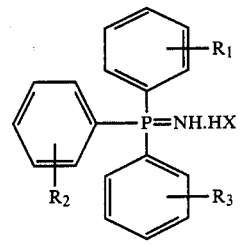

wherein $R_1$, $R_2$ and $R_3$ are each at the ortho or meta position and are selected from hydrogen and alkyl($C_1$–$C_3$), and X is an acid addition salt; processes for producing them, compositions containing them, and methods for using them in mammals to effect diuresis; to lower plasma renin levels and to increase cardiac contractility.

13 Claims, No Drawings

ESTER OF (TRIARYLPHOSPHORANYLIDENE)CARBAMIC ACID HAVING DIURETIC AND ABILITY TO LOWER PLASMA RENIN PROPERTIES

SUMMARY OF THE INVENTION

This invention is concerned with new compounds of the formula:

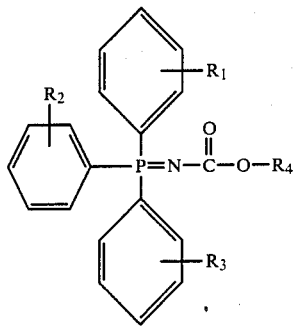

FORMULA I wherein $R_1$, $R_2$ and $R_3$ are each at the ortho or meta position, represent mono- or disubstituents and are selected from the group consisting of hydrogen, alkyl(-$C_1$-$C_3$), alkoxy($C_1$-$C_3$), trifluoromethyl and halogen; and $R_4$ is selected from the group consisting of alkyl(-$C_1$-$C_3$), alkenyl($C_2$-$C_3$), alkynyl($C_2$-$C_4$), cycloalkyl(-$C_3$-$C_5$), cycloalkyl($C_3$-$C_6$)methyl, 4-oxopentyl, 3-tetrahydrofuranyl, 2,3-dihydro-1$\underline{H}$-inden-1-yl, 1-alkyl(-$C_1$-$C_3$)cyclopentyl, trans-2-alkyl($C_1$-$C_3$)cyclopentyl, trans-2-alkoxy($C_1$-$C_3$)cyclopentyl, 1-cyclopropylethyl, 2-methylcyclopropylmethyl, dicyclopropylmethyl, 2-, 3- or 4-pyridinylmethyl, 2-cyclopenten-1-yl, tetrahydro-2$\underline{H}$-pyran-4-yl and cis and trans-2-methoxycyclohexyl; with the proviso that when $R_4$ is alkyl($C_1$-$C_3$), two of $R_1$, $R_2$ and $R_3$ are not hydrogen.

East German Pat. No. 137,716 covers a process for preparing N-substituted triorganophosphine imines which are stated to possess undisclosed biological utility. That patent discloses compounds of the above formula where $R_1$, $R_2$ and $R_3$ are all hydrogen and $R_4$ is alkyl. Therefore, the proviso for $R_4$ eliminates these compounds from the generic formula of this invention. The method of treatment and composition of matter aspects of this invention include these compounds, however.

$R_4$ is preferably methyl, ethyl, 2-, 3-, or 4-pyridinylmethyl, 3-tetrahydrofuranyl or cyclopropylmethyl. In one preferred embodiment, $R_1$ is 2-methyl, 2-ethyl, 2-chloro, 2-bromo, 2-fluoro or 2-trifluoromethyl and $R_2$ and $R_3$ are both hydrogen. In a second preferred embodiment $R_1$ and $R_2$ are the same and are 2-methyl or 2-chloro and $R_3$ is hydrogen. In another preferred embodiment $R_1$ is 3-chloro and $R_2$ and $R_3$ are both hydrogen.

This invention is also concerned with new compounds of the formula:

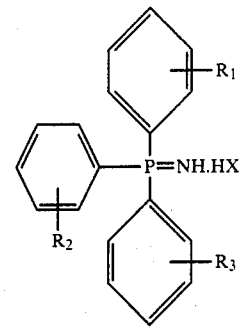

FORMULA II wherein $R_1$, $R_2$ and $R_3$ are each at the ortho or meta position and are hydrogen or alkyl($C_1$-$C_3$); and X is an acid-addition salt such as sulfuric.

This invention is also concerned with a method for effecting diuresis and lowering plasma renin activity in mammals as well as pharmaceutical compositions of matter containing these compounds and with processes for the preparation of these compounds.

DETAILED DESCRIPTION OF THE INVENTION

In accordance with the present invention, there is provided a novel means of effecting diuresis, lowering plasma renin activity and increasing cardiac contractility in a mammal which comprises administering to said mammal a therapeutically effective amount of a compound selected from those of the above described Formula I.

The compounds of Formula I find utility as diuretics and cardiotonics in mammals and as such may be used as the drug of choice for the treatment of edema caused by cardiac, hepatic, pulmonary and renal diseases, as well as drug-induced fluid and salt retention. These compounds may also be useful as hypotensive agents upon chronic administration by virtue of their diuretic activity. As cardiotonic agents, these compounds may likewise be useful in the treatment of congestive heart failure.

Renin is a proteolytic enzyme which converts plasma angiotensinogen to angiotensin I. Angiotensin I, in turn is, enzymatically converted to angiotensin II, which constricts blood vessels and stimulates aldosterone production by the adrenal cortex, and latter leading to increased renal sodium retention and potassium excretion and expansion of extracellular volume.

The action of the currently available diuretics can be depicted by the following diagram:

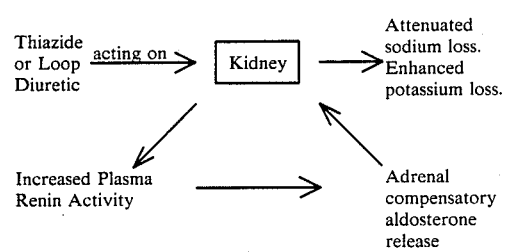

In contrast, the compounds of the present invention acting on the kidney lower plasma renin activity, thereby effecting non-attenuated sodium loss and minimal potassium loss mediated in part by lack of adrenal compensatory aldosterine release.

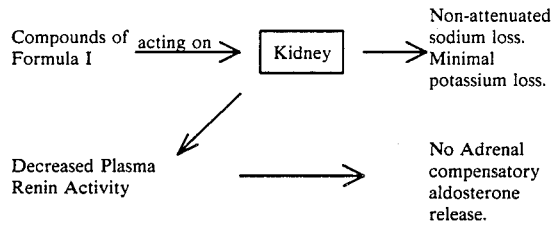

The compounds of this invention may be prepared as described in the following flowcharts and text.

Flowchart A

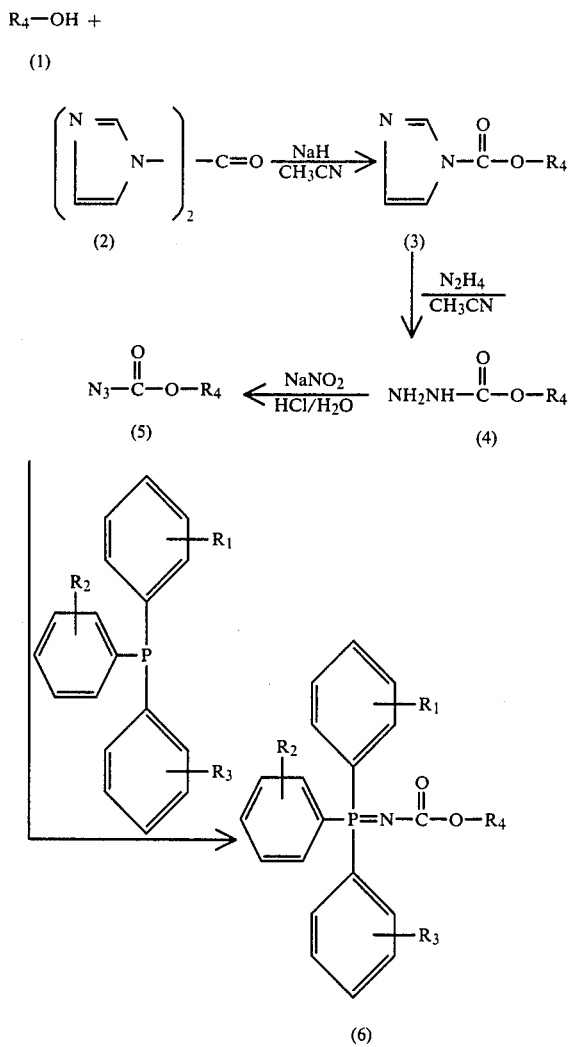

In accordance with Flowchart A, an alcohol (1), where R₄ is alkyl(C₁–C₃), 2-propenyl or tetrahydro-3-furanyl, is reacted with a small portion of sodium hydride in dry acetonitrile until gas evolution ceases and then with carbonyldiimidazole (2) for 2–6 hours, giving the compounds (3), which are then reacted with hydrazine in acetonitrile for 8–24 hours at room temperature and evaporated to dryness, giving the hydrazine derivatives (4) which are then dissolved in a mixture of water and hydrochloric acid, cooled to 0°–5° C. and reacted with sodium nitrite, then extracted into ether as the azide derivatives (5) and finally reacted with a substituted triaryl phosphine, where R₁, R₂ and R₃ are as described above, in ether for 1–4 hours at room temperature, giving the products (6), where R₄ is as described above.

Flowchart B

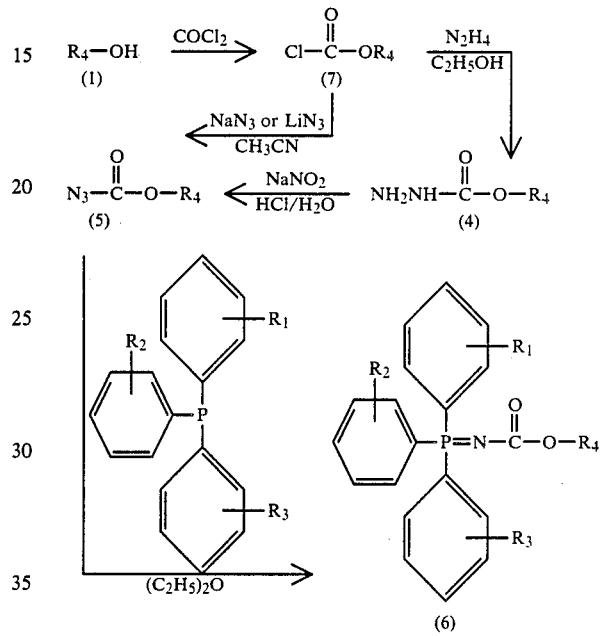

In accordance with Flowchart B, an alcohol (1), where R₄ is alkyl(C₁–C₃), 2-propenyl or tetrahydro-3-furanyl, is reacted with phosgene to give the compounds (7) which may then either be reacted with hydrazine to give (4) and then with sodium nitrite to give (5), or may be reacted with sodium or lithium azide in acetonitrile to give (5) directly, followed by conversion to the products (6) as described in Flowchart A.

Flowchart C

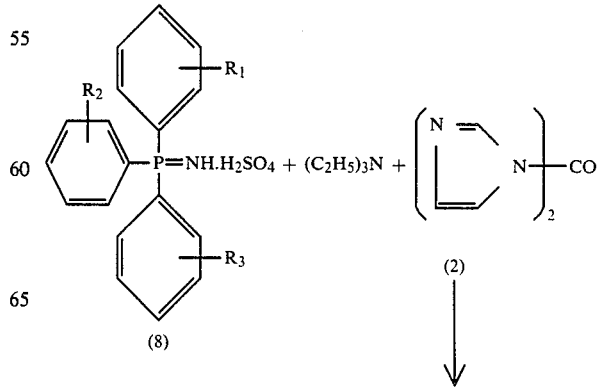

-continued
Flowchart C

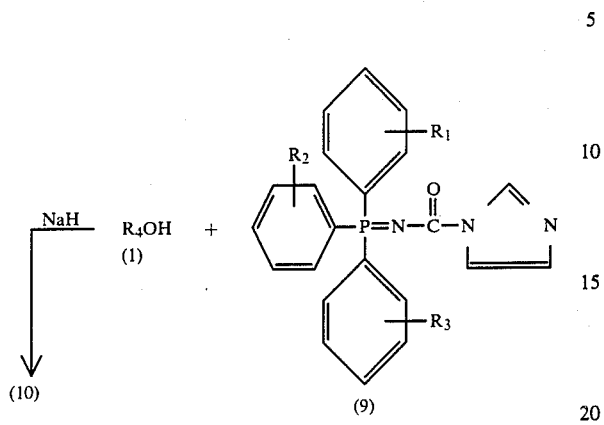

In accordance with Flowchart C, a P,P,P-triphenylphosphine imide sulfate (8), where $R_1$, $R_2$ and $R_3$ are a described above, and triethylamine in tetrahydrofuran reacted with carbonyldiimidazole (2), giving an N-(triphenylphosphoranylidene)-1H-imidazole-1-carboxamide (9) which is then reacted with an alcohol (1), where $R_4$ is as described above, and sodium hydride in 1,2-dimethoxyethane, giving the products (10).

Flowchart D

In accordance with Flowchart D a phosphine (11), where $R_1$, $R_2$ and $R_3$ are as described above, is reacted with a carbonazidate (5), where $R_4$ is as described above, in ether, giving the products (10).

Flowchart E

In accordance with flowchart E, (the process of preparing phosphinimides described in "Houben-Weyl Methoden der Organischen Chemie", 4th Edition, Phosphor Verbindungen II, M. Regitz, ed.) a substituted triaryl phosphine, where $R_1$, $R_2$ and $R_3$ are each at the ortho or meta position and are hydrogen or alkyl($C_1$–$C_3$) is reacted with O-hydroxylaminesulfonic acid in methanol, giving the phosphinimide sulfate salt. The sulfates may be easily converted to other acid-addition salts by simple chemistry.

It is generally preferred that the respective product of each process step described in the above reaction schemes be separated and/or isolated prior to its use as starting material for subsequent steps. Separation and

Lowering of Plasma Renin Activity in Normal Conscious Rats

Compounds were tested for their ability to lower plasma renin activity of conscious, male Wistar rats (180-200 g, Charles River Labs.). Test agents were compounded in a mortar and pestle with 3% preboiled starch suspension. Rats were dosed orally by gavage with 25 mg/kg test agent in a dose volume of 2 ml/kg. At time zero and ⅓, 1, 3 and 6 hours relative to dosing, rats were sacrificed by decapitation and the first 3 seconds of blood collected in two chilled Vacutainer® tubes (Becton-Dickinson, Rutherford, N.J.) containing 40 µl of 150 mg/ml tripotassium EDTA. Plasma fractions, obtained by centrifugation for 20 minutes at 4° C. and 3000 G, were incubated (one of each pair at 37° C., the other at 4° C.) at pH 6.8 in 50 mM phosphate buffer to produce angiotensin I. The incubates contained peptidase inhibitors to prevent angiotensin I degradation and the buffer contained one mg/ml lysozyme (Sigma Grade III) used as an antiabsorbant. The incubates were diluted 20 fold in cold Tris buffer (pH adjusted to 7.4 with glacial acetic acid) also containing one mg/ml lysozyme, and then frozen. Diluted incubates were assayed within 3 days for angiotensin I content by radioimmunoassay according to a modification of the method of Haber, et al., J. Clin. Endocrin., 29, 1349-1355 (1969). Renin activity is calculated as the rate of production of angiotensin I (nanograms of angiotensin I/ml plasma/hour at 37° C.) less controls (rate at 4° C.). The results of this test on a representative compound of this invention appear in Table I.

TABLE I

Percent Lowering of Plasma Renin Activity in Normal Concious Rats at Various Time Intervals Following Administration of a Single 25 mg/kg Oral Dose of (Triphenylphosphoranylidene)carbamic Acid, Ethly Ester

| Hours After Dose | No. of Rats | % Lowering |
|---|---|---|
| 0 | 6 | 0 |
| 1/3 | 6 | 38 |
| 1 | 6 | 74 |
| 3 | 6 | 59 |
| 6 | 6 | 40 |

Inhibition of evoked increase of plasma renin activity was determined by the following test.

Compounds were tested for their ability to prevent drug-induced elevation of plasma renin activity (PRA) in concious, male Wistar rats (180-200 g, Charles River Lab.). PRA elevation was induced by a combined oral provacative treatment (C) of hydrochlorothiazide (10 mg/kg) and 1-(3-benzoyl-3-mercapto-2-methylpropionyl)-L-proline, acetate (U.S. Pat. No. 4,226,775) (one mg/kg), prepared by compounding in a mortar and pestle with preboiled 3% starch suspension. This treatment provided the daily maximum PRA. The daily minimum PRA was obtained from rats given oral starch suspension (S) alone. The magnitude of drug effect on PRA elevation was ascertained from rats pretreated orally with test agent (D), at the indicated doses, 30 minutes prior to administration of provacative treatment (C). The test agent was also compounded in preboiled 3% starch suspension. The dose volumes for both pretreatment and provacative treatment were 2 ml/kg. One hour after provocative treatment the rats were sacrificed by decapitation and the first 3 seconds of blood collected in two chilled Vacutainer® tubes (Becton-Dickinson, Rutherford, N.J.) containing 40 µl of 150 mg/ml tripotassium EDTA. The plasma fractions, obtained by centrifugation for 20 minutes at 4° C. and 3000 G, were incubated (one of each pair at 37° C., the other at 4° C.) at pH 6.8 in 50 mM phosphate buffer to produce angiotensin I. The incubates contained peptidase inhibitors to prevent angiotensin I degradation and the incubation buffer contained one mg/ml lysozyme (Sigma Grade III) used as an antiabsorbant. The incubates were diluted 20 fold in cold 100 mM Tris buffer (pH adjusted to 7.4 with glacial acetic acid) also containing one mg/ml lysozyme, and then frozen. Diluted incubates were assayed within 3 days for angiotensin I content by radioimmunoassay according to a modification of the method of Haber, et al., J. Clin. Endocrin., 29, 1349-1355 (1969).

PRA is calculated as follows:

$$PRA(\text{ng } AI/\text{hour/ml plasma}) = PRA\ 37°\ C. - PRA\ 4°\ C.$$

Percent inhibition of PRA elevation is calculated as follows:

$$\%\ \text{Inhibition} = 100 \times \frac{[PRA(C) - PRA(D)]}{[PRA(C) - PRA(S)]}.$$

The results of this test on representative compounds of this invention appear in Table II.

TABLE II

Percent Inhibition of Plasma Renin Elevation

| Compound | Dose (mg/kg) | Average % Inhibition (No. of Rats) |
|---|---|---|
| (Triphenylphosphoranylidene)carbamic acid, ethyl ester | 25 | 80 (14) |
| | 15 | 79 (6) |
| | 10 | 81 (6) |
| | 7 | 46 (5) |
| | 5 | 29 (5) |
| | 3 | 22 (5) |
| (Triphenylphosphoranylidene)carbamic acid, methyl ester | 25 | 72 (3) |
| (Triphenylphosphoranylidene)carbamic acid, propyl ester | 25 | 90 (3) |
| (Triphenylphosphoranylidene)carbamic acid, tetrahydro-3-furanyl ester | 100 | 85 (8) |
| | 50 | 49 (8) |
| | 25 | 69 (5) |
| (Triphenylphosphoranylidene)carbamic acid 2-propenyl ester | 25 | 67 (3) |
| [(2-Methylphenyl)diphenylphosphoranylidene]carbamic acid, ethyl ester | 25 | 92 (3) |
| (Triphenylphosphoranylidene)carbamic acid, 3-pyridinylmethyl ester | 25 | 40 (3) |
| [(2-Methylphenyl)diphenylphosphoranylidene]carbamic acid, tetrahydro-3-furanyl ester | 25 | 93 (3) |
| [Bis(2-methylphenyl)phenylphosphoranylidene]carbamic acid, ethyl ester | 25 | 54 (3) |
| [(2-Methylphenyl)diphenylphosphoranylidene]carbamic acid, 3-pyridinylmethyl ester | 25 | 75 (3) |
| [Diphenyl[2-(trifluoromethyl)phenyl]phosphoranylidene]carbamic acid, ethyl ester | 25 | 75 (3) |
| [(2-Methylphenyl)diphenylphosphoranylidene]carbamic | 25 | 72 (3) |

TABLE II-continued

Percent Inhibition of Plasma Renin Elevation

| Compound | Dose (mg/kg) | Average % Inhibition (No. of Rats) |
|---|---|---|
| acid, cyclopropylmethyl ester | | |
| [(2-Chlorophenyl)diphenylphosphoranylidene]carbamic acid, ethyl ester | 25 | 96 (3) |
| [(2,6-Dimethylphenyl)diphenylphosphoranylidene]carbamic acid, methyl ester | 25 | 68 (3) |
| [(2-Chlorophenyl)diphenylphosphoranylidene]carbamic acid, methyl ester | 25 | 98 (3) |
| [Diphenyl[2-(trifluoromethyl)phenyl]phosphoranylidene]carbamic acid, methyl ester | 25 | 49 (2) |

The diuretic activity of the compounds of this invention was also determined according to the method of Chan, P. S. and Poorvin, D., Sequential method for combined screening antihypertensive and diuretic agents in the same spontaneously hypertensive rat. Clinical and Experimental Hypertension, 1(6), 817-830 (1979).

Male spontaneously hypertensive rats (SHR) of Okamoto strain, 16 weeks old, Taconic Farms Inc. were used in the test. These rats were kept on Purina laboratory chow and tap water ad libitum for 8 weeks before use. One male adult rat (about 300 g) was dosed by gavage with a test compound at 100 mg/kg together with 0.9% sodium chloride loading at 25 ml/kg at zero hour. The test compound was suspended in 3% pre-boiled starch at 50 mg/ml. The rat was put in a metabolism cage. The 0-5 hour urine was collected and urinary sodium and potassium were determined using a Beckman Astra 4. The effects of representative compounds of the invention according to this test appear in Table III expressed in milliequivalents (mEQ) of urinary sodium and potassium excreted.

TABLE III

Diuretic Activity in Spontaneously Hypertensive Rats

| Compound | Volume ml | Sodium mEQ/5 Hours | Potassium mEQ/5 Hours |
|---|---|---|---|
| (Triphenylphosphoranylidene)carbamic acid, ethyl ester | 15.5 | 1.86 | 0.50 |
| (Triphenylphosphoranylidene)carbamic acid, methyl ester | 23.3 | 2.53 | 0.55 |
| (Triphenylphosphoranylidene)carbamic acid, n-propyl ester | 12.5 | 1.37 | 0.48 |
| (Triphenylphosphoranylidene)carbamic acid, tetrahydro-3-furanyl ester | 14.8 | 1.10 | 0.70 |
| (Triphenylphosphoranylidene)carbamic acid, 2-propenyl ester | 13.3 | 1.17 | 0.67 |
| (Triphenylphosphoranylidene)carbamic acid, 4-oxopentyl ester | 13.3 | 1.16 | 0.58 |
| (Triphenylphosphoranylidene)carbamic acid, cyclobutylmethyl ester | 14.5 | 1.47 | 0.60 |
| (Triphenylphosphoranylidene)carbamic acid, 2,3-dihydro-1H—inden-1-yl ester | 13.0 | 1.41 | 0.87 |
| (Triphenylphosphoranylidene)carbamic acid, 1-methylcyclopentyl ester | 14.8 | 1.49 | 0.86 |
| (Triphenylphosphoranylidene)carbamic acid, trans-methylcyclopentyl ester | 14.3 | 1.55 | 0.68 |
| (Triphenylphosphoranylidene)carbamic acid, 2-propynyl ester | 15.5 | 1.76 | 0.58 |
| (Triphenylphosphoranylidene)carbamic acid, 1-ethylcyclopentyl ester | 12.5 | 1.34 | 1.01 |
| (Triphenylphosphoranylidene)carbamic acid, cyclopropylmethyl ester | 19.5 | 2.00 | 0.57 |
| (Triphenylphosphoranylidene)carbamic acid, trans-2-methoxycyclopentyl ester | 17.0 | 1.83 | 0.72 |
| (Triphenylphosphoranylidene)carbamic acid, 2-butynyl ester | 10.0 | 1.15 | 0.57 |
| [(2-Methylphenyl)diphenylphosphoranylidene]carbamic acid, ethyl ester | 25.5 | 2.68 | 0.78 |
| [(2-Methoxyphenyl)diphenylphosphoranylidene]carbamic acid, ethyl ester | 11.3 | 1.31 | 0.97 |
| (Triphenylphosphoranylidene)carbamic acid, 1-cyclopropylethyl ester | 12.0 | 1.19 | 0.65 |
| (Triphenylphosphoranylidene)carbamic acid, 2-pyridinylmethyl ester | 14.0 | 1.25 | 0.82 |
| (Triphenylphosphoranylidene)carbamic acid, 2-cyclopenten-1-yl ester | 15.5 | 1.58 | 0.83 |
| (Triphenylphosphoranylidene)carbamic acid, trans-2-ethoxycyclopentyl ester | 13.3 | 1.38 | 0.73 |
| (Triphenylphosphoranylidene)carbamic acid, 4-pyridinylmethyl ester | 16.5 | 1.50 | 0.70 |
| (Triphenylphosphoranylidene)carbamic acid, 1-propylcyclopentyl ester | 10.3 | 1.14 | 0.63 |
| (Triphenylphosphoranylidene)carbamic acid, 2-pyridinylmethyl ester | 14.5 | 1.60 | 1.00 |
| (Triphenylphosphoranylidene)carbamic acid, (2-methylcyclopropyl)methyl ester | 11.3 | 1.28 | 0.47 |
| (Triphenylphosphoranylidene)carbamic acid, tetrahydro-2H—pyran-4-yl ester | 15.3 | 1.60 | 0.64 |
| [(2-Methylphenyl)diphenylphosphoranylidene]carbamic acid, tetrahydro-3-furanyl ester | 22.3 | 2.71 | 0.97 |
| (Triphenylphosphoranylidene)carbamic acid, cis and trans-2-methoxycyclohexyl ester | 11.3 | 1.15 | 0.59 |
| (Triphenylphosphoranylidene)carbamic acid, trans-2-methoxycyclohexyl ester | 12.8 | 1.45 | 0.67 |
| (Triphenylphosphoranylidene)carbamic acid, dicyclopropylmethyl ester | 14.3 | 1.58 | 1.07 |
| [Bis(2-methylphenyl)phenylphosphoranylidene]carbamic acid, | 14.5 | 1.46 | 0.73 |

TABLE III-continued

Diuretic Activity in Spontaneously Hypertensive Rats

| Compound | Volume ml | Sodium mEQ/5 Hours | Potassium mEQ/5 Hours |
|---|---|---|---|
| ethyl ester | | | |
| [(2-Methylphenyl)diphenylphosphoranylidene]carbamic acid, 3-pyridinylmethyl ester | 12.3 | 1.48 | 0.62 |
| [Diphenyl[2-(trifluoromethyl)phenyl]phosphoranylidene]carbamic acid, ethyl ester | 19.3 | 2.12 | 0.91 |
| [(2-Methylphenyl)diphenylphosphoranylidene]carbamic acid, cyclopropylmethyl ester | 12.0 | 1.33 | 0.73 |
| [(2-Chlorophenyl)diphenylphosphoranylidene]carbamic acid, ethyl ester | 19.5 | 2.05 | 0.71 |
| [(2-Methylphenyl)diphenylphosphoranylidene]carbamic acid, cyclopentyl ester | 10.8 | 1.18 | 0.67 |
| [[(2,6-Dimethylphenyl)diphenyl]phosphoranylidene]carbamic acid, ethyl ester | 13.0 | 1.48 | 0.86 |
| [(2-Ethylphenyl)diphenylphosphoranyidene]carbamic acid, ethyl ester | 19.0 | 2.07 | 0.78 |
| [(2-Methylphenyl)diphenylphosphoranylidene]carbamic acid, methyl ester | 18.3 | 1.95 | 0.88 |
| [(2,6-Dimethylphenyl)diphenylphosphoranylidene]carbamic acid, methyl ester | 12.8 | 1.33 | 0.84 |
| [(2-Chlorophenyl)diphenylphosphoranylidene]carbamic acid, methyl ester | 20.0 | 2.30 | 0.94 |
| [Diphenyl[2-(trifluoromethyl)phenyl]phosphoranylidene]carbamic acid, methyl ester | 18.5 | 1.71 | 1.02 |
| [Diphenyl[2-(trifluoromethyl)phenyl]phosphoranylidene]carbamic acid, tetrahydro-3-furanyl ester | 16.3 | 1.64 | 0.63 |
| [(2-Chlorophenyl)diphenylphosphoranylidene]carbamic acid, tetrahydro-3-furanyl ester | 20.0 | 1.90 | 0.68 |
| [Bis(2-methylphenyl)phenylphosphoranylidene]carbamic acid, methyl ester | 13.5 | 1.45 | 0.76 |
| [(2-Ethylphenyl)diphenylphosphoranylidene]carbamic acid, methyl ester | 14.3 | 1.36 | 0.58 |
| [(3-Chlorophenyl)diphenylphosphoranylidene]carbamic acid, ethyl ester | 23.8 | 2.32 | 0.64 |
| [(3-Chlorophenyl)diphenylphosphoranylidene]carbamic acid, methyl ester | 23.0 | 2.45 | 0.60 |
| [Bis(2-chlorophenyl)phenylphosphoranylidene]carbamic acid, ethyl ester | 22.3 | 2.40 | 0.38 |
| (Triphenylphosphoranylidene)carbamic acid, cyclopentyl ester | 14.0 | 1.48 | 0.80 |
| [(2-Bromophenyl)diphenylphosphoranylidene]carbamic acid, ethyl ester | 22.5 | 2.51 | 0.68 |
| [(3-Trifluoromethylphenyl)phosphoranylidene]carbamic acid, ethyl ester | 13.5 | 1.38 | 0.67 |
| [bis(3-Chlorophenyl)phenylphosphoranylidene]carbamic acid, ethyl ester | 18.3 | 1.84 | 0.89 |
| [(3-Fluorophenyl)diphenylphosphoranylidene]carbamic acid, ethyl ester | 24.0 | 2.44 | 0.62 |
| [(2,3-Dichlorophenyl)diphenylphosphoranylidene]carbamic acid ethyl ester | 14.3 | 1.83 | 0.86 |
| [Bis(2-methylphenyl)phenylphosphoranylidene]carbamic acid, methyl ester | 13.5 | 1.45 | 0.76 |
| [Diphenyl(2-fluorophenyl)phosphoranylidene]carbamic acid, ethyl ester | 19.8 | 2.01 | 0.66 |
| [[2-(1-Methylethyl)phenyl]diphenylphosphoranylidene]carbamic acid, ethyl ester | 18.8 | 2.08 | 0.83 |
| [(3-Bromophenyl)diphenylphosphoranylidene]carbamic acid, ethyl ester | 12.4 | 1.16 | 0.78 |
| (Triphenylphosphoranylidene)carbamic acid, 3-pyridinylmethyl ester | 14.5 | 1.60 | 1.00 |
| (2-Methylphenyl)diphenylphosphinimide sulfate | 16.3 | 1.88 | 0.68 |
| Triphenylphosphinimide sulfate | 12.0 | 1.25 | 0.65 |
| [Bis(2-methylphenyl)phenyl]phosphinimide sulfate | 13.0 | 1.44 | 0.88 |

The effect of (triphenylphospharnylidene)carbamic acid, ethyl ester on cardiac contractility was determined by the following test.

Isolated rat hearts were prepared and perfused essentially as described by Neely and Rovetto, Techniques for perfusing isolated rat hearts., in Methods of Enzymology, 24, part D, 43–60 (1975), J. G. Hardman and B. W. O'Malley (eds.), Academic Press, New York, N.Y. The hearts were cooled in ice cold saline and transferred to a Langendorff apparatus and perfused in a retrograde fashion with oxygenated Krebs-Henseleit buffer at 37° C. A 2-0 silk thread was secured to the left ventricular apex and run via pulleys to a force displacement transducer (Grass Instrument Co., model FT03C). Force of contraction (F), the first derivative of force with respect to time (dF/dt), and rate of cardiac contraction (HR) were monitored on a polygraph recorder (Grass Instrument Co., model 7D).

The perfusion medium was a modified Krebs-Henseleit buffer of the following composition:

| Sodium chloride | 119 mM |
|---|---|
| Potassium chloride | 4.7 mM |
| Calcium chloride | 2.54 mM |
| Monobasic sodium phosphate | 1.19 mM |
| Magnesium sulfate | 1.19 mM |
| Glucose | 5.5 mM |
| Sodium bicarbonate | 25 mM |

This medium was equilibrated with 95% oxygen:5% carbon dioxide at 37° C.

(Triphenylphosphoranylidene)carbamic acid, ethyl ester was dissolved in absolute ethanol at a concentration of 10 mg/ml and then diluted with Krebs-Henseleit buffer to the required stock concentration. The stock solution was infused at a constant rate by a syringe pump into the flow of buffer presented to the isolated heart at a rate necessary to achieve the desired final concentration. The results of this test appear in Table IV.

TABLE IV

Cardiodynamic Effects of (Triphenylphosphoranylidene)-carbamic Acid, Ethyl Ester in the Isolated Perfused Rat Heart Preparation

| Final Drug Concentration (mg/liter) | No. of Rat Hearts | Concentration Force (g) (mean % change) | dF/dt(g/sec) (mean % change) | HR (mean % change) |
|---|---|---|---|---|
| 1 | 7 | 5 | 6 | −3 |
| 4 | 6 | 18 | 16 | −2 |
| 8 | 5 | 24 | 21 | −2 |

The same effect has been achieved in anesthetized dogs by the intravenous administration of (triphenylphospharanylidene)carbamic acid, ethyl ester.

The compounds of the present invention have been found to be highly useful for lowering plasma renin activity, as diuretics and as cardiotonic agents in mammals when administered in amounts ranging from about 1.0 mg to about 50.0 mg/kg of body weight per day. A preferred dosage regimen for optimum results would be from about 3.0 mg to about 20.0 mg/kg of body weight per day. Such dosage units are employed that a total of from about 200 mg to about 1400 mg of active compound for a subject of about 70 kg of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. The compounds of this invention are preferably administered orally but may be administered in any convenient manner such as by the intravenous, intramuscular or subcutaneous routes, in appropriate quantities.

The active compounds of the present invention may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of tablets, troches, capsules, elixirs, suspensions, syrups, wafers, and the like. Such compositions and preparations should contain at least 0.1% of active compound. The percentage of the compositions and preparations may, of course, be varied and may conveniently be between about 2% to about 60% of the weight of the unit. The amount of active compound in such therapeutically useful compositions is such that a suitable dosage will be obtained.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propyl parabens as preservatives, a dye and flavoring such as cherry or orange flavor. Of course, any material used in preparing these dosage forms must be pharmaceutically pure and non-toxic.

The invention will be described in greater detail in conjunction with the following non-limiting examples.

EXAMPLE 1

(Triphenylphosphoranylidene)carbamic acid, ethyl ester

A 26.0 g portion of ethyl carbazate was dissolved in 150 ml of ice/water and 25 ml of concentrated hydrochloric acid and stirred with ice bath cooling as 18 g of sodium nitrite in 50 ml of water was added dropwise during 20 minutes. This mixture was stirred in an ice bath for 2 hours then extracted with 250 ml of dichloromethane. The organic layer was separated, dried over magnesium sulfate and evaporated in vacuo at 30° C. to yield ethyl carbonazidate as a mobile liquid. This liquid was dissolved in 100 ml of ether, filtered and the filtrate added to a filtered solution of 66 g of triphenylphosphine in 400 ml of ether. This mixture was stirred vigorously (gas evolution) for one hour. The precipitate was collected, washed with ether and dried, giving 50.8 g of the desired literature product, mp. 135°–137° C.

EXAMPLE 2

(Triphenylphosphoranylidene)carbamic acid, methyl ester

The subject compound was prepared by the procedure of Example 1, using methyl carbonazidate in place of ethyl carbonazidate. It melted at 138°–139° C.

EXAMPLE 3

(Triphenylphosphoaranylidene)carbamic acid, n-propyl ester

A 12.2 g portion of n-propyl chloroformate in 150 ml of acetonitrile was stirred at 5°–10° C. as 7.0 g of sodium azide was added. This mixture was stirred for 18 hours and then filtered. The filtrate containing the n-propyl carbonazidate was stirred as a filtered solution of 24 g of triphenylphosphine in 200 ml of ether was added. This solution was stirred for 2 hours (gas evolution), then evaporated to an oil in vacuo at 30° C. This oil was stirred with 200 ml of ether for ½ hour; the crystalline product was collected, washed with two 75 ml portions of ether and dried, giving 14.1 g of the desired product, mp 90°–91° C.

EXAMPLE 4

(Triphenylphosphoranylidene)carbamic acid, tetrahydro-3-furanyl ester

A 4.4 g portion of 3-hydroxytetrahydrofuran was dissolved in 200 ml of dry acetonitrile. The solution was stirred as 100 mg of 50% sodium hydride in oil was added. This mixture was stirred until gas evolution ceased, then 8.1 g of carbonyldiimidazole was added. The mixture was stirred at room temperature for 3 hours. A solution of 1.8 g of 95% hydrazine in 100 ml of acetonitrile was prepared, dried over magnesium sulfate and added to the above solution of tetrahydro-3-furanyl 1-imidazole carboxylate, which was then stirred at room temperature overnight. This mixture was evaporated in vacuo at 40° C. to a glassy residue containing tetrahydro-3-furanyl carbonazidate. This solid was dissolved in a mixture of 150 ml of water and 15 ml of concentrated hydrochloric acid, cooled to 0±2° C. and stirred as a solution of 4 g of sodium nitrite in 50 ml of water was added dropwise. This mixture was stirred for 30 minutes at 0°–5° C. after addition was complete and then extracted with 150 ml of ether. The ether extract containing tetrahydro-3-furanyl carbonazidate was washed with 75 ml of saturated aqueous sodium bicarbonate, dried over magnesium sulfate and then added to a filtered solution of 13 g of triphenylphosphine in 150 ml of ether, with stirring (gas evolution). The mixture was stirred for 2 hours at room temperature, then the precipitate was collected, washed with 100 ml of ether and dried in vacuo at 60° C., giving 7.0 g of the desired product, mp 130°–131° C.

Following the general procedure of Example 4, using the indicated starting materials, the products of Examples 5-7, found in Table V, were prepared.

TABLE V

| Ex. | Starting Material | Product | MP° C. |
|---|---|---|---|
| 5 | 2-propen-1-ol | (triphenylphosphoranylidene)carbamic acid, 2-propenyl ester | 108–109 |
| 6 | cyclopentanol | (triphenylphosphoranylidene)carbamic acid, cyclopentyl ester | 126–127 |
| 7 | 4-oxopentan-1-ol | (triphenylphosphoranylidene)carbamic acid, 4-oxo-pentan-1-yl ester | 73–75 |

EXAMPLE 8

(Triphenylphosphoranylidene)carbamic acid, cyclopropylmethyl ester

A mixture consisting of 0.75 g of cyclopropylmethanol, 0.48 g of 50% sodium hydride in mineral oil, and 50 ml of 1,2-dimethoxythane was stirred at room temperature for a few minutes, and then treated with 3.7 g of N-(triphenylphosphoranylidene)-1H-imidazole-1-carboxamide.

The reaction mixture was stirred under reflux conditions for 6 hours, and then poured into 300 ml of ice-water. The precipitate was collected, washed with water, and dried in vacuo over phosphorus pentoxide at room temperature. Thin-layer chromatographic studies indicated that a single compound was present, but recrystallization from diethyl ether was also useful. A yield of 3.2 g of the desired compound was obtained, mp 107°–113° C.

Following the general procedure of Example 8, using other starting materials in place of cyclopropylmethanol, the products of Examples 9-26 were obtained. In a few cases, preliminary purification by chromatography on silica gel, using a mixture of hexane and ethyl acetate as a developing solvent, was employed.

TABLE VI

| Ex. | Starting Material | Product | MP °C. |
|---|---|---|---|
| 9 | trans-2-methylcyclopentanol | (triphenylphosphoranylidene)carbamic acid, trans-2-methylcyclopentyl ester | 101–109 |
| 10 | 2-propyn-1-ol | (triphenylphosphoranylidene)carbamic acid, 2-propynyl ester | 103–106 |
| 11 | 1-ethylcyclopentanol | (triphenylphosphoranylidene)carbamic acid, 1-ethylcyclopentyl ester | 84–90 |
| 12 | 2,3-dihydro-1H—inden-1-ol | (triphenylphosphoranylidene)carbamic acid, 1,2,3-dihydro-1H—inden-1-yl ester | 124–128 |
| 13 | trans-2-methoxycyclopentanol | (triphenylphosphoranylidene)carbamic acid, trans-2-methoxycyclopentyl ester | 95–101 |
| 14 | 2-butyne-1-ol | (triphenylphosphoranylidene)carbamic acid, 2-butynyl ester | 125–129 |
| 15 | 1-cyclopropylethanol | (triphenylphosphoranylidene)carbamic acid, 1-cyclopropylethyl ester | 79–84 |
| 16 | 2-cyclopenten-1-ol | (triphenylphosphoranylidene)carbamic acid, 2-cyclopenten-1-yl ester | 110–114 |
| 17 | trans-2-ethoxycyclopentanol | (triphenylphosphoranylidene)carbamic acid, trans-2-ethoxycyclopentyl ester | 116–118 |
| 18 | 1-propylcyclopentanol | (triphenylphosphoranylidene)carbamic acid, 1-propylcyclopentyl ester | 107–114 |
| 19 | 2-methylcyclopropanemethanol | (triphenylphosphoranylidene)carbamic acid, (2-methylcyclopropyl)methyl ester | 91–94 |
| 20 | tetrahydro-2H—pyran-4-ol | (triphenylphosphoranylidene)carbamic acid, tetrahydro-2H—pyran-4-yl ester | 138–142 |
| 21 | cis and trans-2-methoxycyclohexanol | (triphenylphosphoranylidene)carbamic acid, cis- and trans-2-methoxycyclohexyl ester | 92–98 |
| 22 | trans-2-methoxycyclohexanol | (triphenylphosphoranylidene)carbamic acid, trans-2-methoxycyclohexyl ester | 98–100 |
| 23 | 2-pyridinylmethanol | (triphenylphosphoranylidene)carbamic acid, 2-pyridinylmethyl ester | 86–88 |
| 24 | 4-pyridinylmethanol | (triphenylphosphoranylidene)carbamic acid, 4-pyridinylmethyl ester | 150–152 |
| 25 | 3-pyridinylmethanol | (triphenylphosphoranylidene)carbamic acid, 3-pyridinylmethyl ester | 108–110 |
| 26 | dicyclopropylmethanol | (triphenylphosphoranylidene)carbamic acid, dicyclopropylmethyl ester | 129–133 |

EXAMPLE 27

[(2-Methylphenyl)diphenylphosphoranylidene]carbamic acid, 3-pyridinylmethyl ester A mixture of 9.2 g of diphenyl(2-methylphenyl)phosphine in 65 ml of methanol was heated to solution on a steam bath, then cooled to room temperature. Over 5 minutes, a solution of 3.76 g of hydroxylamine-O-sulfonic acid in 24 ml of methanol was added. The mixture was filtered into 400 ml of ether and the solid collected giving 8.40 g of P-(2-methylphenyl)-P,P-diphenylphosphine imide, sulfate salt.

The 8.40 g of the above compound was reacted with triethylamine and carbonyldiimidazole in tetrahydrofuran as described in Example 8, giving 5.35 g of 1-[[[(2-methylphenyl)diphenylphosphoranylidene]amino]carbonyl]-1H-imidazole.

A 760 mg portion of 3-pyridinemethanol, 35 ml of 1,2-dimethoxyethane, 340 mg of 50% sodium hydride in oil and 2.7 g of 1-[[[(2-methylphenyl)diphenylphosphoranylidene]amino]carbonyl]-1H-imidazole were reacted as described in Example 8, giving 2.05 g of the desired product, mp 142°–143° C.

Following the procedure of Example 27, using starting materials other than 3-pyridinemethanol, the products of Examples 28–30, foumd in Table VII, were obtained.

TABLE VII

| Ex. | Starting Material | Product | MP °C. |
|---|---|---|---|
| 28 | cyclopropyl-methanol | [(2-methylphenyl)diphenylphosphoranylidene]carbamic acid, cyclopropylmethyl ester | 110–112 |
| 29 | cyclopentanol | [(2-methylphenyl)diphenylphosphoranylidene]carbamic acid, cyclopentyl ester | 166–168 |
| 30 | 2-propyn-1-ol | [(2-methylphenyl)diphenylphosphoranylidene]carbamic acid, 2-propyn-1-ol ester | 112–115 |

EXAMPLE 31

[(2-Methoxyphenyl)diphenylphosphoranylidene]carbamic acid, ethyl ester

A 1.0 g portion of (2-methoxyphenyl)diphenylphosphine was added to 30 ml of ether and stirred. The mixture was filtered and to the filtrate was added 3.6 ml of 1M ethyl carbonazidate in ether. This mixture was repeatedly concentrated, treated with fresh ether and refrigerated, giving 400 mg of the desired product, mp 80°–83° C.

EXAMPLE 32

[(2-Methylphenyl)diphenylphosphoranylidene]carbamic acid, tetrahydro-3-furanyl ester A 2.76 g portion of (2-methylphenyl)diphenylphosphine was stirred in 60 ml of ether, then treated with charcoal and filtered. To the filtrate was added a solution of 1.7 g tetrahydro-3-furanyl carbonazidate in 60 ml of ether. After standing 8 hours the solid was collected, washed with ether and dried, giving 2.3 g of the desired product, mp 118°–119° C.

EXAMPLE 33

[(2-Methylphenyl)diphenylphosphoranylidene]carbamic acid, ethyl ester

A solution of 1.0 g of (2-methylphenyl)diphenylphosphine in 30 ml of ether was treated with 4 ml of 1M ethyl carbonazidate in ether. The mixture was allowed to stand 48 hours, then repeatedly concentrated and finally treated with fresh ether and refrigerated, giving 930 mg of the desired compound, mp 113°–114° C.

Following the procedure of Example 33, using the indicated phosphine and carbonazidate derivatives, the products of Examples 34–57, found in Table VIII were obtained.

TABLE VIII

| Ex. | —Phosphine | —Carbonazidate | Product | MP °C. |
|---|---|---|---|---|
| 34 | [2-(trifluoromethyl)-phenyl]diphenyl- | ethyl- | [diphenyl[2-(trifluoromethyl)phenyl]phosphoranylidene]carbamic acid, ethyl ester | glass |
| 35 | [2-(trifluoromethyl)-phenyl]diphenyl- | methyl- | [diphenyl[2-(trifluoromethyl)phenyl]phosphoranylidene]carbamic acid, methyl ester | 135–140 |
| 36 | [2-(trifluoromethyl)-phenyl]diphenyl- | tetrahydro-3-furanyl- | [diphenyl[2-(trifluoromethyl)phenyl]phosphoranylidene]carbamic acid, tetrahydro-3-furanyl ester | 102–104 |
| 37 | (2-ethylphenyl)-diphenyl- | methyl- | [(2-ethylphenyl)diphenylphosphoranylidene]carbamic acid, methyl ester | 121–122 |
| 38 | (2,6-dimethylphenyl)-diphenyl- | methyl- | [(2,6-dimethylphenyl)diphenylphosphoranylidene]carbamic acid, methyl ester | 149–151 |
| 39 | (2-methylphenyl)-diphenyl- | methyl- | [(2-methylphenyl)diphenylphosphoranylidene]carbamic acid, methyl ester | 139–142 |
| 40 | (2-chlorophenyl)-diphenyl- | ethyl- | [(2-chlorophenyl)diphenylphosphoranylidene]carbamic acid, ethyl ester | 110–112 (dec.) |
| 41 | (2-chlorophenyl)-diphenyl- | tetrahydro-3-furanyl- | [(2-chlorophenyl)diphenylphosphoranylidene]carbamic acid, tetrahydro-3-furanyl ester | 118–120 (dec.) |
| 42 | (3-chlorophenyl)-diphenyl- | ethyl- | [(3-chlorophenyl)diphenylphosphoranylidene]carbamic acid, ethyl ester | 103–107 |
| 43 | (3-chlorophenyl)-diphenyl- | methyl- | [(3-chlorophenyl)diphenylphosphoranylidene]carbamic acid, methyl ester | 99.5–100 (dec.) |
| 44 | bis(2-chlorophenyl)-phenyl- | ethyl- | [bis(2-chlorophenyl)phenylphosphoranylidene]carbamic acid, ethyl ester | 144–146 |
| 45 | (2-chlorophenyl)-diphenyl- | methyl- | [(2-chlorophenyl)diphenylphosphoranylidene]carbamic acid, methyl ester | 140–144 |

TABLE VIII-continued

| Ex. | —Phosphine | —Carbon-azidate | Product | MP °C. |
|---|---|---|---|---|
| 46 | bis(2-methylphenyl)phenyl- | ethyl- | [bis(2-methylphenyl)phenylphosphoranylidene]carbamic acid, ethyl ester | 130–133 |
| 47 | [(2,6-dimethylphenyl)diphenyl]- | ethyl- | [[(2,6-dimethylphenyl)diphenyl]phosphoranylidene]carbamic acid, ethyl ester | 119–120 |
| 48 | (2-bromophenyl)diphenyl- | ethyl- | [(2-bromophenyl)diphenylphosphoranylidene]carbamic acid, ethyl ester | 113–114 |
| 49 | (3-fluorophenyl)diphenyl- | ethyl- | [[(3-fluorophenyl)diphenylphosphoranylidene]carbamic acid, ethyl ester | 112–115 |
| 50 | (2-ethylphenyl)diphenyl- | ethyl- | [(2-ethylphenyl)diphenylphosphoranylidene]carbamic acid, ethyl ester | 87–89 |
| 51 | bis(3-chlorophenyl)phenyl- | ethyl- | [[bis(3-chlorophenyl)phenyl]phosphoranylidene]carbamic acid, ethyl ester | 108–109 |
| 52 | (3-trifluoromethyl)phenyl-diphenyl- | ethyl- | [(3-trifluorophenyl)diphenylphosphoranylidene]carbamic acid, ethyl ester | 85–87 |
| 53 | (2,3-dichlorophenyl)diphenyl- | ethyl- | [(2,3-dichlorophenyl)diphenylphosphoranylidene]carbamic acid ethyl ester | 134–136 |
| 54 | Diphenyl(2-fluorophenyl)- | ethyl- | [Diphenyl(2-fluorophenyl)phosphoranylidene]carbamic acid, ethyl ester | 106–108 |
| 55 | 2-[(1-Methylethyl)phenyl]diphenyl- | ethyl- | [[2-(1-Methylethyl)phenyl]diphenylphosphoranylidene]carbamic acid, ethyl ester | 134–136 |
| 56 | (3-Bromophenyl)diphenyl- | ethyl- | [(3-Bromophenyl)diphenylphosphoranylidene]carbamic acid, ethyl ester | 123–124 |
| 57 | [Bis(2-methylphenyl)phenyl- | methyl- | [Bis(2-methylphenyl)phenylphosphoranylidene]carbamic acid, methyl ester | 140–142 |

EXAMPLE 58

(2-Methylphenyl)diphenylphosphinimide sulfate

Five grams of (2-methylphenyl)diphenylphosphine was dissolved in 35 ml of methanol by warming. Cooling to room temperature gave a suspension which was treated with a solution of 2 g of O-hydroxylaminesulfonic acid in 13 ml of methanol. A slight exothermic reaction resulted, the temperature rising from 22° C. to 29° C. during twenty minutes. After returning to room temperature, the reaction mixture was filtered into 220 ml of diethyl ether (vigorous stirring), resulting in the formation of a crystalline precipitate. This was filtered off, washed with diethyl ether, and dried, giving 3.4 g of the desired compound, mp 194°–196° C.

EXAMPLE 59

Triphenylphosphinimide sulfate

The subject compound was prepared by the procedure of Example 58, triphenylphosphine replacing the (2-methylphenyl)diphenylphosphine. It melted at 184°–190° C. with decomposition.

EXAMPLE 60

[Bis(2-methylphenyl)phenyl]phosphinimide sulfate

The subject compound was prepared by the procedure of Example 58, bis(2-methylphenyl)phenylphosphine relacing the (2-methylphenyl)diphenylphosphine. It melted at 194°–196° C.

EXAMPLE 61

Preparation of Compressed Tablet

| Ingredient | mg/Tablet |
|---|---|
| (Triphenylphosphoranylidene-carbamic acid, ethyl ester | 5–100 |
| Dibasic Calcium Phosphate NF | qs |
| Starch USP | 40 |
| Modified Starch | 10 |
| Magnesium Stearate USP | 1–5 |

EXAMPLE 62

Preparation of Hard Shell Capsule

| Ingredient | mg/Capsule |
|---|---|
| (Triphenylphosphoranylidene)-carbamic acid, methyl ester | 5–100 |
| Lactose, Spray Dried | qs |
| Magnesium Stearate | 1–10 |

EXAMPLE 63

Intravenous Solutions

An organic such as citric, succinic, tartaric or mixtures thereof is dissolved in water at a concentration of 0.1–0.75%. (Triphenylphosphoranylidene)carbamic acid, ethyl ester is dissolved in the acid-water mixture providing a clear solution which, after sterilization, is suitable for intravenous administration.

EXAMPLE 64

Intramuscular Preparations (Triphenylphosphoranylidene)carbamic acid, ethyl ester is dissolved in one of the following solvents or cosolvents and then sterilized, providing solutions for intramuscular administration.

| | |
|---|---|
| Benzyl alcohol | |
| Olive oil | |
| Peanut oil | |
| Propylene glycol/water | 20–80% |
| Polyethylene glycol 300/water | 20–100% |
| Polyethylene glycol 400/water | 20–100% |
| Polyethylene glycol 4000/water | 0.2–0.5% |
| Ethanol/water | 20–50% |

EXAMPLE 65

Oral Preparations (Triphenylphosphoranylidene)carbamic acid, ethyl ester is dissolved in one of the following systems providing solutions or suspensions for oral administration.

| | |
|---|---|
| Sodium lauryl sulfate/water | 0.5–3% |
| Polysorbate 80/water | 0.5–5% |
| Polysorbate 40/water | 0.01–0.75% |
| Polysorbate 20/water | 0.005–0.02% |
| Polyoxyethylene lauryl ether/water | 0.5–4% |
| Polyoxyethylene stearyl ether/water | 0.5–4% |
| Polyoxyethylene oleyl ether/water | 0.5–4% |

EXAMPLE 66

Oral Suspension

The following formulation provides an acceptable oral suspension.

| | |
|---|---|
| (Triphenylphosphoranylidene)-carbamic acid, ethyl ester | 1–5% |
| Veegum | 0.1–2.0% |
| Methyl paraben | 0.08% |
| Propyl paraben | 0.02% |
| Sucrose/Sorbitol | 20–80% |
| Flavor | qs |
| Water qs to | 100% |

What is claimed is:

1. A compound selected from those of the formula:

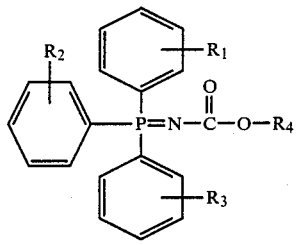

wherein $R_1$, $R_2$ and $R_3$ are each at the ortho or meta position, represent mono- or disubstituents selected from the group consisting of hydrogen, alkyl($C_1$–$C_3$), alkoxy($C_1$–$C_3$), trifluoromethyl and halogen; and $R_4$ is selected from the group consisting of alkyl($C_1$–$C_3$), alkenyl($C_2$–$C_3$), alkynyl($C_2$–$C_4$), cycloalkyl($C_3$–$C_5$), cycloalkyl($C_3$–$C_6$)methyl, 4-oxopentyl, 2,3-dihydro-1H-inden-1-yl, 1-alkyl($C_1$–$C_3$)cyclopentyl, trans-2-alkyl($C_1$–$C_3$)cyclopentyl, trans-2-alkoxy($C_1$–$C_3$)cyclopentyl, 1-cyclopropylethyl, 2-methylcyclopropylmethyl, dicyclopropylmethyl, 2-cyclopenten-1-yl, and cis and trans-2-methoxycyclohexyl; with the proviso that when $R_4$ is alkyl($C_1$–$C_3$), two of $R_1$, $R_2$ and $R_3$ are not hydrogen.

2. A compound according to claim 1, wherein $R_4$ is methyl, ethyl, or cyclopropylmethyl.

3. A compound according to claim 2, wherein $R_1$ is 3-chloro.

4. The compound according to claim 2, [[bis(3-chlorophenyl)phenyl]phosphoranylidene]carbamic acid, ethyl ester.

5. A compound according to claim 2, wherein $R_1$ and $R_2$ are the same and are 2-methyl or 2-chloro and $R_3$ is hydrogen.

6. A compound according to claim 5 which is:
[bis(2-chlorophenyl)phenylphosphoranylidene]carbamic acid, ethyl ester; or
[bis(2-methylphenyl)phenylphosphoranylidene]carbamic acid, methyl ester.

7. A compound according to claim 1, which is [(2-methylphenyl)diphenylphosphoranylidene]carbamic acid, tetrahydro-3-furanyl ester.

8. A compound according to claim 2 (triphenylphosphoranylidene)carbamic acid, cyclopropylmethyl ester.

9. The compound according to claim 1, (triphenylphosphoranylidene)carbamic acid, 2-propynyl ester.

10. A method for effecting diuresis in a mammal which comprises administering to said mammal a diuretic effective amount of a compound selected from those of the formula:

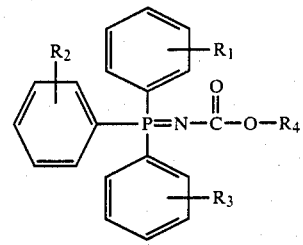

wherein $R_1$, $R_2$ and $R_3$ are each at the ortho or meta position, represent mono- or disubstituents selected from the group consisting of hydrogen, alkyl($C_1$–$C_3$), alkoxy($C_1$–$C_3$), trifluoromethyl and halogen; and $R_4$ is selected from the group consisting of alkyl($C_1$–$C_3$), alkenyl($C_2$–$C_3$), alkynyl($C_2$–$C_4$), cycloalkyl($C_3$–$C_5$), cycloalkyl($C_3$–$C_6$)methyl, 4-oxopentyl, 2,3-dihydro-1H-iden-1-yl, 1-alkyl($C_1$–$C_3$)cyclopentyl, trans-2-alkyl($C_1$–$C_3$)cyclopentyl, trans-2-alkoxy($C_1$–$C_3$)cyclopentyl, 1-cyclopropylethyl, 2-methylcyclopropylmethyl, dicyclopropylmethyl, 2-cyclopenten-1-yl, and cis and trans-2-methoxycyclohexyl.

11. A method for lowering plasma renin activity in a mammal which comprises administering to said mammal a plasma renin lowering effective amount of a compound selected from those of the formula:

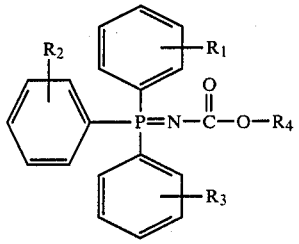

wherein $R_1$, $R_2$ and $R_3$ are each at the ortho or meta position, represent mono- or disubstituents selected from the group consisting of hydrogen, alkyl($C_1$–$C_3$), alkoxy($C_1$–$C_3$), trifluoromethyl and halogen; and $R_4$ is selected from the group consisting of alkyl($C_1$–$C_3$), alkenyl($C_2$–$C_3$), alkynyl($C_2$–$C_4$), cycloalkyl($C_3$–$C_5$), cycloalkyl($C_3$–$C_6$)methyl, 4-oxopentyl, 2,3-dihydro-1H-iden-1-yl, 1-alkyl($C_1$–$C_3$)cyclopentyl, trans-2-alkyl(-

$C_1$–$C_3$)cyclopentyl, trans-2-alkoxy($C_1$–$C_3$)cyclopentyl, 1-cyclopropylethyl, 2-methylcyclopropylmethyl, dicyclopropylmethyl, 2-cyclopenten-1-yl, and cis and trans-2-methoxycyclohexyl.

12. A method for increasing cardiac contractility in a mammal which comprises administering to said mammal a cardiotonicity-potentiating effective amount of a compound selected from those of the formula:

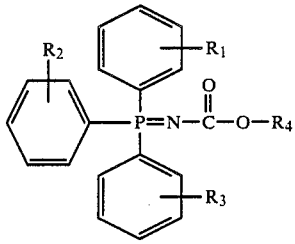

wherein $R_1$, $R_2$, and $R_3$ are each at the ortho or metal position, represent mono- or disubstituents selected from the group consisting of hydrogen, alkyl($C_1$–$C_3$), alkoxy($C_1$–$C_3$), trifluoromethyl and halogen; and $R_4$ is selected from the group consisting of alkyl($C_1$–$C_3$), alkenyl($C_2$–$C_3$), alkynyl($C_2$–$C_4$), cycloalkyl($C_3$–$C_5$), cycloalkyl($C_3$–$C_6$)methyl, 4-oxopentyl, 2,3-dihydro-1H-iden-1-yl, 1-alkyl($C_1$–$C_3$)cyclopentyl, trans-2-alkyl($C_1$–$C_3$)cyclopentyl, trans-2-alkoxy($C_1$–$C_3$)cyclopentyl, 1-cyclopropylethyl, 2-methylcyclopropylmethyl, dicyclopropylmethyl, 2-cyclopenten-1-yl, and cis and trans-2-methoxycyclohexyl.

13. A pharmaceutical composition of matter in dosage unit form comprising an effective amount of a compound selected from those of the formula:

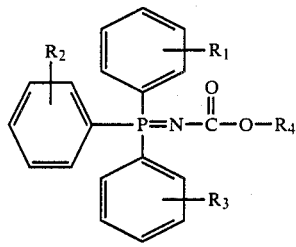

wherein $R_1$, $R_2$ and $R_3$ are each at the ortho or meta position, represent mono- or disubstituents selected from the group consisting of hydrogen, alkyl($C_1$–$C_3$), alkoxy($C_1$–$C_3$), trifluoromethyl and halogen; and $R_4$ is selected from the group consisting of alkyl($C_1$–$C_3$), alkenyl($C_2$–$C_3$), alkynyl($C_2$–$C_4$), cycloalkyl($C_3$–$C_5$), cycloalkyl($C_3$–$C_6$)methyl, 4-oxopentyl, 2,3-dihydro-1H-inden-1-yl, 1-alkyl($C_1$–$C_3$)cyclopentyl, trans-2-alkyl($C_1$–$C_3$)cyclopentyl, trans-2-alkoxy($C_1$–$C_3$)cyclopentyl, 1-cyclopropylethyl, 2-methylcyclopropylmethyl, dicyclopropylmethyl, 2-cyclopenten-1-yl, and cis and trans-2-methoxycyclohexyl with a proviso that when $R_4$ is alkyl($C_1$–$C_3$), two of $R_1$, $R_2$ and $R_3$ are not hydrogen in association with a pharmaceutically acceptable carrier.

* * * * *